(12) United States Patent
Koza et al.

(10) Patent No.: US 12,303,110 B2
(45) Date of Patent: May 20, 2025

(54) METHOD AND SYSTEM FOR GUIDING AN INTRA-ORAL SCAN

(71) Applicant: DENTSPLY SIRONA inc., York, PA (US)

(72) Inventors: André Koza, Lorsch (DE); Ronny Kucharczyk, Worms (DE)

(73) Assignee: Dentsply Sirona Inc., York, PA (US)

( * ) Notice: Subject to any disclaimer, the term of this patent is extended or adjusted under 35 U.S.C. 154(b) by 671 days.

(21) Appl. No.: 17/425,964

(22) PCT Filed: Jan. 29, 2020

(86) PCT No.: PCT/US2020/015635
§ 371 (c)(1),
(2) Date: Jul. 27, 2021

(87) PCT Pub. No.: WO2020/160119
PCT Pub. Date: Aug. 6, 2020

(65) Prior Publication Data
US 2022/0192800 A1 Jun. 23, 2022

(30) Foreign Application Priority Data
Jan. 30, 2019 (EP) .................................... 19000056

(51) Int. Cl.
A61B 1/24 (2006.01)
A61B 1/00 (2006.01)
(Continued)

(52) U.S. Cl.
CPC .......... *A61B 1/24* (2013.01); *A61B 1/000094* (2022.02); *A61B 1/00048* (2013.01);
(Continued)

(58) Field of Classification Search
CPC .......... A61B 1/24; A61B 1/000094–96; A61B 1/00048; A61B 1/00055; A61B 1/00172;
(Continued)

(56) References Cited

U.S. PATENT DOCUMENTS 11,628,046 B2 * 4/2023 Elbaz ................. A61B 1/00016
433/29
11,647,909 B2 * 5/2023 Van Der Poel ...... A61B 5/0077
433/29
(Continued)

FOREIGN PATENT DOCUMENTS

EP 3689218 A1 8/2020
EP 3689218 B1 10/2023
WO WO-2020160119 A1 8/2020

OTHER PUBLICATIONS

"European Application Serial No. 19000056.2, Extended European Search Report mailed Aug. 1, 2019", 8 pgs.
(Continued)

*Primary Examiner* — Wesner Sajous
(74) *Attorney, Agent, or Firm* — SCHWEGMAN LUNDBERG & WOESSNER, P.A.

(57) ABSTRACT

A method, system and computer readable storage media for guiding an intra-oral scan utilizing augmented reality. By visualizing a scan strategy in a field of view of a clinician during an intra-oral scanning scan procedure, a need to monitor the progress of the intra-oral scan on a separate monitor may be eliminated or reduced in order to save time.

17 Claims, 8 Drawing Sheets

(51) Int. Cl.
  *A61B 5/00* (2006.01)
  *A61C 9/00* (2006.01)
  *G06T 19/00* (2011.01)
(52) U.S. Cl.
  CPC ...... *A61B 1/00055* (2013.01); *A61B 1/00172* (2013.01); *A61B 1/00194* (2022.02); *A61B 5/4547* (2013.01); *A61B 5/742* (2013.01); *A61C 9/0053* (2013.01); *G06T 19/006* (2013.01)
(58) Field of Classification Search
  CPC ....... A61B 5/4547; A61B 5/742; A61B 34/25; A61C 9/0053; A61C 1/0023; A61C 1/084; A61C 7/002; A61C 9/004; A61C 5/40; A61C 19/004; G06T 19/006; G06T 2200/24; G06T 2210/41; G06T 7/20; G06T 7/11; G06T 7/70; G06T 7/0012; G06T 7/33; G06T 3/40; G06T 2200/04; G06T 2207/30036; G06T 2207/30201; G06T 2207/30204; G06T 2207/10116; G06F 3/011; G06F 3/0334; G06F 3/04815
  See application file for complete search history.

(56) References Cited

U.S. PATENT DOCUMENTS

| | | | |
|---|---|---|---|
| 11,672,629 B2* | 6/2023 | Chekh | A61C 7/002 382/130 |
| 2002/0082498 A1 | 6/2002 | Wendt et al. | |
| 2015/0350517 A1 | 12/2015 | Duret et al. | |
| 2016/0191887 A1 | 6/2016 | Casas | |
| 2016/0331493 A1 | 11/2016 | Kopelman et al. | |
| 2017/0056136 A1* | 3/2017 | Adamson | A61B 1/00055 |
| 2017/0202633 A1 | 7/2017 | Liu | |
| 2018/0168780 A1 | 6/2018 | Kopelman | A61C 1/082 |
| 2021/0045843 A1* | 2/2021 | Pokotilov | G16H 20/40 |
| 2022/0096004 A1* | 3/2022 | Koza | A61B 5/0816 |
| 2022/0192800 A1* | 6/2022 | Koza | A61B 1/00172 |
| 2023/0181020 A1* | 6/2023 | Pesach | A61B 5/0088 348/46 |
| 2023/0263397 A1* | 8/2023 | Van Der Poel | A61B 5/0077 433/29 |
| 2023/0414322 A1* | 12/2023 | Chekh | A61C 7/002 |
| 2024/0046490 A1* | 2/2024 | Lang | A61C 5/40 |
| 2024/0081952 A1* | 3/2024 | Pokotilov | G16H 50/20 |

OTHER PUBLICATIONS

"European Application Serial No. 19000056.2, Response filed Feb. 5, 2021 to Extended European Search Report mailed Aug. 1, 2019", 49 pgs.

"International Application Serial No. PCT/US2020/015635, International Preliminary Report on Patentability mailed Aug. 12, 2021", 7 pgs.

"International Application Serial No. PCT/US2020/015635, International Search Report mailed May 5, 2020", 3 pgs.

"International Application Serial No. PCT/US2020/015635, Written Opinion mailed May 5, 2020", 5 pgs.

* cited by examiner

METHOD AND SYSTEM FOR GUIDING AN INTRA-ORAL SCAN

CROSS-REFERENCE TO RELATED APPLICATIONS

This is a National Phase application of International Application No. PCT/US2020/015635, filed on Jan. 29, 2020 which claims the benefit of and priority to European Patent Application Number 19000056.2, filed on Jan. 30, 2019, which are herein incorporated by reference for all purposes.

TECHNICAL FIELD

The present application generally relates to a method, a system and a computer readable storage media for guiding an intraoral scan and, more particularly, to a method, system and a computer readable storage media for visualizing a scan strategy in a patient's mouth.

BACKGROUND OF THE INVENTION

Users of intra-oral cameras may determine by an alteration in an audio output if a scanning process has been interrupted. To check whether all necessary areas of an intra-oral cavity have been scanned, the user may turn his/her head away from the scanning site to visually look at a display/monitor showing a three-dimensional (3D) reconstruction of scanned areas of the cavity. It may therefore be useful to have a procedure wherein a user may continue to look in a patient's mouth during intra-oral scanning without having to turn away to a monitor to view a 3D reconstruction of a jaw or strategy for scanning the jaw.

U.S. Patent Application Publication No. 2017/0056136A1 discloses a method for performing an optical three-dimensional recording wherein scanning instructions are displayed on a monitor that is away from a scanning site for user to view.

U.S. Patent Application No. 2017202633 discloses an imaging and display system for guiding medical interventions comprising a wearable display for viewing by a user wherein the display presents a composite, or combined image that includes pre-operative surgical navigation images, intraoperative images, and in-vivo microscopy images or sensing data.

U.S. Patent Application No. 20020082498 discloses a method for image-guided surgery comprising capturing 3-dimensional (3D) volume data of a portion of a patient, processing the volume data so as to provide a graphical representation of the data, capturing a stereoscopic video view of a scene including a portion of said patient, rendering the graphical representation and the stereoscopic video view in a blended manner so as to provide a stereoscopic augmented image, and displaying said stereoscopic augmented image in a video-see-through display.

U.S. Patent Application Publication No. 20160191887 describes a real-time surgery navigation method and apparatus for displaying an augmented view of a patient from a static or dynamic viewpoint of a surgeon. A surface image, a graphical representation of the internal anatomic structure of the patient processed from preoperative or intraoperative images, and a computer geometrically registering both images may be used. Responsive to geometrically registering the images, a head mounted display may present to a surgeon an augmented view of the patient.

SUMMARY OF THE INVENTION

Existing limitations associated with the foregoing, as well as other limitations, can be overcome by the method according to claim 1, the system according to claim 11 and the computer readable storage media according to claim 12 for the visualization of a strategy for intra-oral scanning.

In an aspect herein, the present invention provides a method for guiding a scan of a jaw utilizing augmented visualization, the method comprising: obtaining a jaw model; providing a scan strategy including the jaw model and a first and second control points; overlaying the scan strategy as an augmentation on a target site through a display device for augmented visualization such that the scan strategy appears directly superimposed on said target site; determining a recording path based on the first and second control points; positioning an intra-oral camera over an area of the jaw corresponding to the first control point; acquiring a plurality of three-dimensional optical recordings by moving the intra-oral camera over the jaw along the determined recording path such that a corresponding region of the jaw defined by the determined recording path is recorded; and registering the plurality of three-dimensional optical recordings into an overall three-dimensional recording.

In another aspect herein, the method further comprises one or more of the steps: (i) wherein the jaw model is a standard three-dimensional jaw model or an ongoing three dimensional reconstruction of scanned teeth, (ii) wherein the standard three-dimensional jaw model is modified to correspond to a tooth situation of a patient, (iii) wherein the standard three-dimensional jaw model and the ongoing three-dimensional reconstruction of scanned teeth are displayed separately in the field of view of the a user of the display device for augmented visualization, (iv) wherein the scan strategy is overlaid to guide a measurement process selected from the group consisting of an occlusal measurement, a lingual measurement, a first step of a buccal measurement, a second step of a buccal measurement, a fringe measurement, a bite block measurement, and a palate measurement (v) wherein the scan strategy is automatically updated in order to record different portions of the jaw, (vi) further comprising determining areas of the plurality of three-dimensional optical recordings that have gaps, and providing additional control points and/or additional recording paths on the scan strategy in succession for further recording, (vii) wherein a success of the registering step is tracked in order to update the scan strategy, (viii) further comprising updating an orientation of the scan strategy in real time based on a tracking system, said tracking system including information from the intra-oral camera, information tracking patient movements and/or information tracking clinician movements, (ix) wherein said target site is a site selected from the group consisting of the actual teeth, or a site in a field of view of a user of the display device for augmented visualization.

In another aspect, a system for guiding a scan of a jaw utilizing augmented visualization is provided, the system comprising: a display device for augmented visualization, and at least one processor configured to perform the steps of; obtaining a jaw model; providing a scan strategy including the jaw model and a first and second control points; overlaying the scan strategy as an augmentation on a target site through a display device for augmented visualization such that the scan strategy appears directly superimposed on said target site; determining a recording path based on the first and second control points; positioning an intra-oral camera over an area of the jaw corresponding to the first control point; acquiring a plurality of three-dimensional optical recordings by moving the intra-oral camera over the jaw along the determined recording path such that a corresponding region of the jaw defined by the determined recording path is recorded; and registering the plurality of three-dimensional optical recordings into an overall three-dimensional recording. In a further aspect, patient and jaw movements is tracked such that gaps resulting from scanning during such movements are filled by a re-scan of corresponding areas of the teeth. Moreover, portions in the overall three-dimensional recording with poor image quality/resolution (inadequate 3D point density) is determined and filled by a re-scan of corresponding areas of the teeth.

In another aspect herein, the system further comprises one or more of the configurations: (i) wherein the jaw model is a standard three-dimensional jaw model or an ongoing three dimensional reconstruction of scanned teeth. (ii) wherein the processor is further configured to modify the standard three-dimensional jaw model to correspond to a tooth situation of a patient, (iii) wherein the processor is further configured to display the standard three-dimensional jaw model and the ongoing three-dimensional reconstruction of scanned teeth separately in a field of view of a user of the display device for augmented visualization, (iv) wherein the processor is further configured to overlay the scan strategy to guide a measurement process, said measurement process being selected from the group consisting of an occlusal measurement, a lingual measurement, a first step of a buccal measurement, a second step of a buccal measurement, a fringe measurement, a bite block measurement and a palate measurement, (v) wherein the processor is further configured to update the scan strategy automatically in order to record different portions of the jaw, (vi) wherein the processor is further configured to perform the steps of determining areas of the plurality of three-dimensional optical recordings that have gaps, and providing additional control points and/or additional recording paths on the scan strategy in succession for further recording, (vii) wherein the processor is further configured to track a success of the registering step in order to update the scan strategy, (viii) further comprising the processor being further configured to perform the step of updating an orientation of the scan strategy in real time based on a tracking system, said tracking system including information from the intra-oral camera, information tracking patient movements and/or information tracking clinician movements, (ix) wherein said target site is a site selected from the group consisting of the actual teeth, or a site in a field of view of a user of the display device for augmented visualization.

In even yet another aspect, a non-transitory computer-readable storage medium is provided, the non-transitory computer-readable storage medium storing a program which, when executed by a computer system, causes the computer system to perform a procedure comprising: obtaining a jaw model; providing a scan strategy including the jaw model and a first and second control points; overlaying the scan strategy as an augmentation on a target site through a display device for augmented visualization such that the patient scan strategy appears directly superimposed on said target site; determining a recording path based on the first and second control points; acquiring a plurality of three-dimensional optical recordings corresponding to a region of the jaw defined by the determined recording path; and registering the plurality of three-dimensional optical recordings into an overall three-dimensional recording.

BRIEF DESCRIPTION OF THE DRAWINGS

Example embodiments will become more fully understood from the detailed description given herein below and the accompanying drawings, wherein.

DETAILED DESCRIPTION OF THE INVENTION

In accordance with example aspects described herein, a method, system and computer readable storage media are provided for proposing and visualizing an optimal scan strategy for intra-oral scans.

System for Guiding an Intra-Oral Scan

Figure 1:
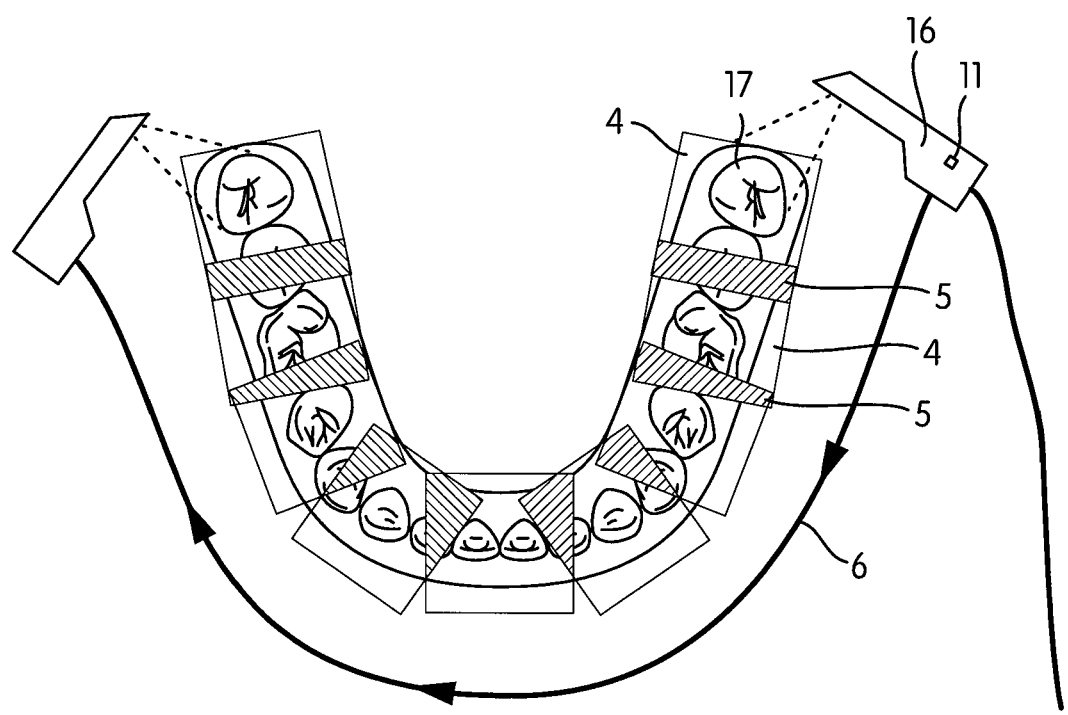
FIG. 1 is a top view illustrating overlapping three-dimensional optical recordings according to an embodiment of the present invention.

During intra-oral scanning, an intra-oral camera 16 (FIG. 1) may automatically record or be manually operated to record a plurality of individual three-dimensional optical recordings 4 in succession at a set frequency during the measurement. The individual three-dimensional optical recordings 4 may then be combined by means of a registration method into an overall three-dimensional recording of a dental subject to be measured. During the measurement, the intra-oral camera 16 may be moved relative to the dental subject (such as a lower jaw or an upper jaw), wherein the three-dimensional optical images are generated at regular time intervals. The individual images can, for example, be generated at a clock frequency between 10 Hz and 20 Hz. The registration may be performed by means of a computer system 100 which may evaluate the individual three-dimensional optical recordings 4 recorded. Iterative Closest Point algorithm (ICP) may be used as the registration method. This algorithm is a known process for registering two-dimensional or three-dimensional subjects. Herein different rotations and translations may be applied to corresponding pairs of points of the two individual three-dimensional optical recordings 4 to be registered, thereby minimizing a quadratic error of the distances between the pairs of points. This iterative convergence may be performed until the two recordings coincide within the overlapping area.

Alternatively, the registration may take place on the basis of the color of the recorded subject, the surface curvature of the recorded subject or on the basis of characteristic geometries of the subject. Given registration on the basis of characteristic geometries, a pattern recognition algorithm may be used wherein the two individual three-dimensional optical recordings 4 to be registered may be searched for a specific geometric pattern, such as for an occlusal surface of a specific tooth.

However, a registration process may include registration errors if, for example, the intra-oral camera moves too quickly in relation to the subject, resulting in the size of the overlapping area 5 being insufficient. Moreover, a focus of the intra-oral camera 16 may not be sharply set, thereby causing the subject to be indistinctly imaged such that the recording quality of the image is insufficient. An additional reason could be that movable objects such as the tongue of the patient or a finger of the treating dentist are recorded during measurement. Consequently, the overlapping areas of the images may not correspond.

Therefore one or more scan strategies 42 may be displayed to a clinician 10 in an augmented fashion (as shown in the visualization system of FIG. 2 and as described hereinafter), wherein different recordings made be acquired separately using optimized recording paths and clusters from the different recordings may be registered to each other in a stable framework for a global registration said global registration being enabled due to the optimized recording paths. The augmented display of the scan strategy 42 in the mouth area may eliminate or substantially eliminate the need for the clinician to look away from the mouth of the patient 14 to a separate screen.

As part of the scan strategy 42, a first control point 13 (FIG. 3a) may be displayed by means of a display device 12 on a jaw model 26 also displayed by means of the display device 12. The intra-oral camera 16 may therefore automatically record a plurality of individual three-dimensional optical recordings 4 during the measurement, for example at a frequency of 18 Hz, wherein individual recordings may not need to be triggered manually as the camera is moved relative to the actual teeth 17. The intra-oral camera 16 may function, for example, according to fringe projection methods or confocal measurement methods.

Figure 2:
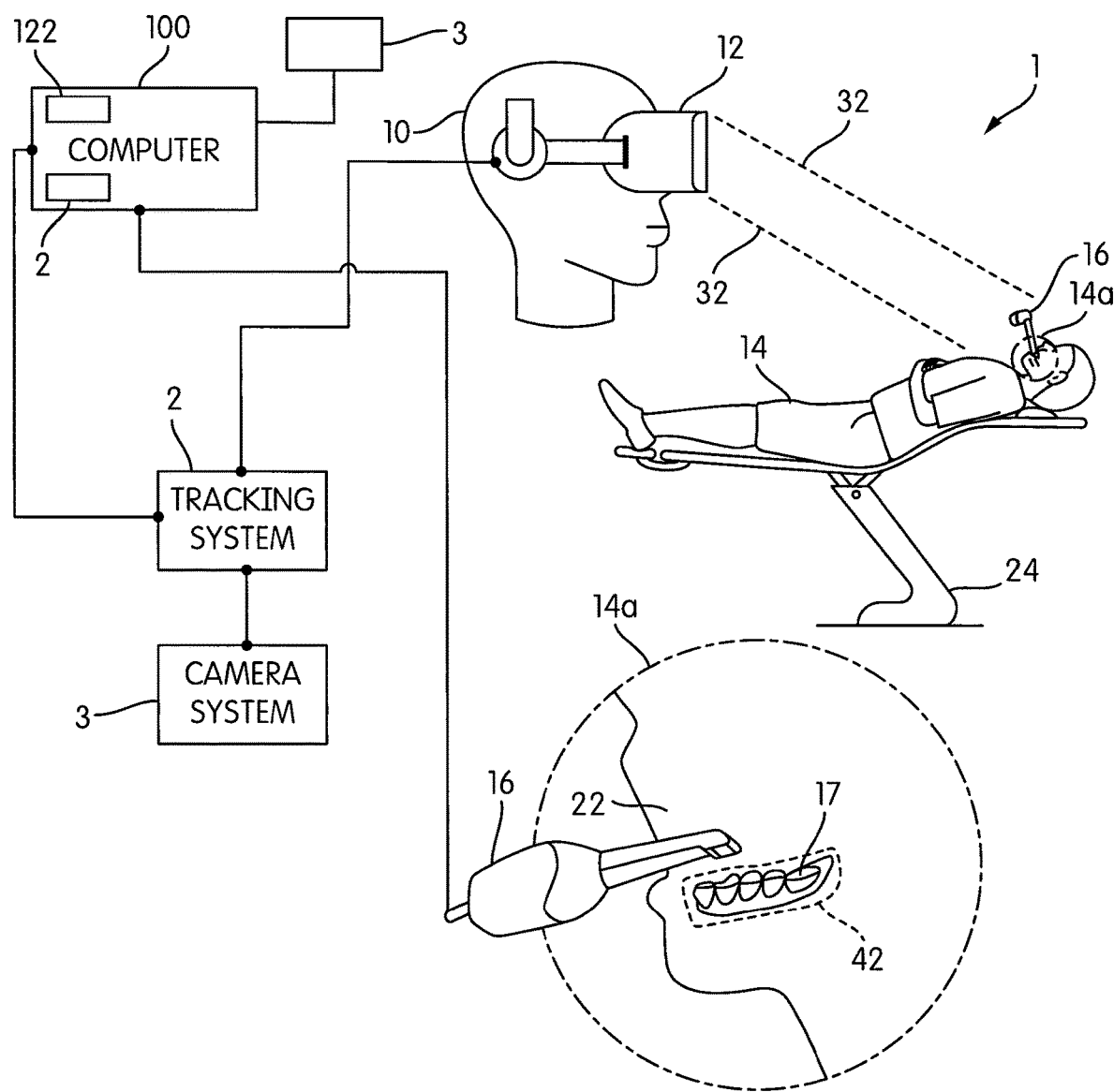
FIG. 2 is a system diagram illustrating a visualization system according to an embodiment of the present invention.
Figure 3A:
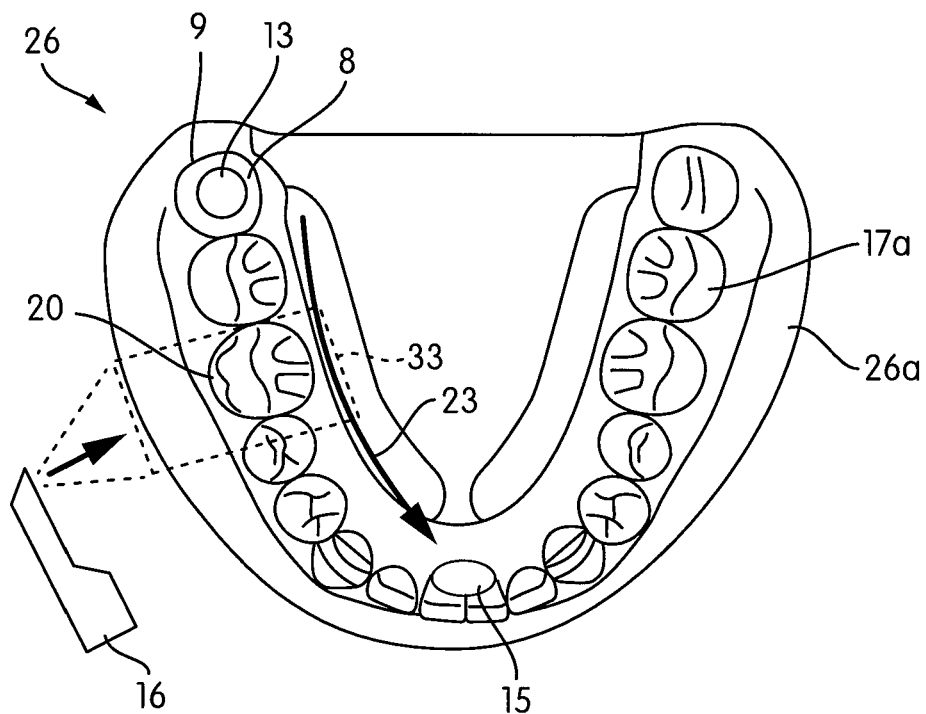
FIG. 3a illustrates a top view of a standard model according to an exemplary embodiment of the present invention.
Figure 3B:
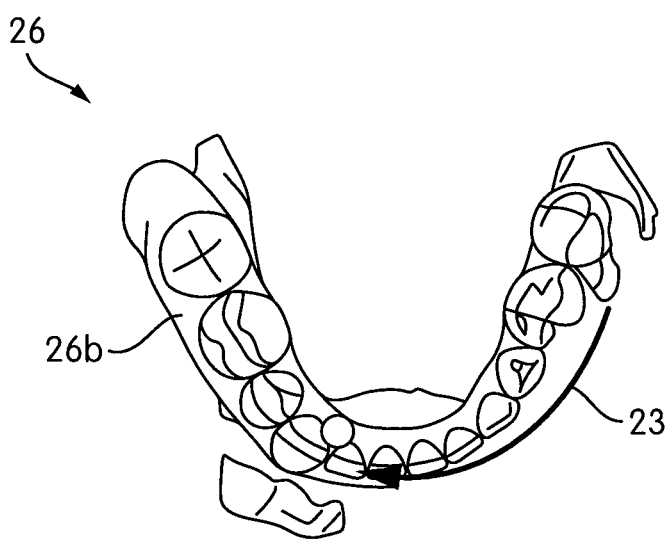
FIG. 3b illustrates top view of a three-dimensional scan according to an exemplary embodiment of the present invention.

FIG. 2 illustrates a visualization system 1 comprising a display device 12 for augmented visualization such as head mounted augmented reality glasses, an HUD display, or a stereoscopic display capable of receiving stereoscopic video images, or otherwise display device 12 that may be used for overlaying the scan strategy 42 (such as, for example a first control point 13, a second control point 15, and or recording path 23 on a jaw model 26 (preferably a three-dimensional jaw model) which may be a standard three-dimensional jaw model 26a or an ongoing three dimensional reconstruction of scanned teeth 26b, FIG. 3a, 3b) in an augmented manner on a target site 14a, (such as on the jaw or actual teeth 17 of a patient 14 or anywhere within a field of view 32 of a clinician 10 who is looking through the display device 12) or on a stereoscopic video of the target site such that the scan strategy 42 appears to be directly superimposed on the target site 14a. A control point may have different forms such as different shapes, sizes, colors, structures etc. and may be any object that defines a start, end or otherwise position of a recording.

Alternatively the scan strategy 42 may be displayed directly on a screen of a smart see-through glass worn by the clinician without being superimposed directly on the target site. Moreover the scan strategy 42 may be automatically updated on an ongoing basis to record different portions of the patient's actual teeth 17. By using the display device 12, the clinician 10 may visualize, where in the intra oral cavity 22 of a patient 14 he/she may start scanning from and the optimal scan strategy including a recording direction may be shown to the clinician 10. A software may indicate on the display device 12, based on predetermined criteria such as an adequate overlap of three-dimensional optical recordings 4, which areas of the jaw are not scanned yet and/or which areas may be rescanned to achieve a complete scan.

The display device 12 may be connected to or form part of a computer system 100. With the aid of the computer system, it may be possible to automatically determine which areas of the registered three-dimensional optical recordings 4 have gaps, such that additional control points and/or additional recording paths may be displayed in succession in these areas on the jaw model 26 for user guidance. Therefore the guidance may take place control point for control point until all gaps are filled.

The computer system 100 (also shown in FIG. 4) may include a tracking system 2 and a processor 122. The tracking system 2 may alternatively be separate from the computer system and may form at least part of any of the devices, components, and/or systems discussed herein. The tracking system 2 may be electrically connected to a processor 122 and may offer real-time location data for a precise location and orientation of images (e.g. scan strategy 42) and objects (e.g. target site 14a) in a common coordinate system. In an exemplary embodiment herein, the tracking system 2 may be vision based, for example as cameras for visual tracking of the patient 14, features of the patient (such as the head or intra-oral cavity), and/or predetermined markers (not shown) placed on the patient 14. Said visual tracking may be achieved using, for example object/pattern recognition. A camera system 3 such as a 3D optical tracking system and/or stereoscopic camera system may be included in the computer system and/or may form or be a part of the tracking system 2. The camera system 3 may also be embedded in the display device 12 of the clinician 10. The camera system may operate under one of several depth sensing principles including, for example, (i) structural light, (ii) Time of Flight (ToF) and/or (iii) stereoscopic principles explained hereinafter. For cameras employing structural light, a light source may be used to project a known pattern onto the patient 14, and a receiver may detect the distortion of the reflected pattern to calculate depth map based on geometry. For cameras employing Time of Flight (ToF) principles, a light source may send out a pulse, and a sensor may detect a reflection of the pulse from the patient 14 in order to record it's time of flight. Knowing that and the constant speed of light, the system may calculate how far away the patient 14 is. Alternatively, a modulated light source may be sent and a phase change of light reflected from the patient may be detected. For cameras employing stereoscopic principles, multiple cameras may be placed at different positions to capture multiple images of the patient, and a depth map may be calculated based on geometry. This depth information may be used to track the patient's location during treatment (e.g. during dental treatment).

The tracking system 2 may also include data from the intra oral camera 16 wherein a success of the registration process may be tracked during intra-oral scanning in order to update the scan strategy 42 when needed.

In an exemplary embodiment of the present invention, scan strategy 42 may optionally be overlaid on a target site 14a after a request is received from the clinician 10 through a user interface 126 of the computer system 100 (such as a gesture recognition system and/or a voice recognition system or the like) before or during a scanning procedure. Overlaying of the scan strategy 42 on the target site 14a through the display 12 may be performed dynamically and in real time and may be achieved by the processor 122 working in tandem with the tracking system 2 wherein changes in position of (i) the patient 14 and/or (ii) the clinician 10, captured by the tracking system 2, may be translated into corresponding changes in positions of the overlaid patient scan strategy 42 such that said scan strategy 42 routed to a screen of the display device 12 appears directly superimposed on the target site 14a of the patient 14 even as the patient 14 and/or or clinician 10 moves. Moreover, responsive to a request from the clinician 10 the processor may be configured to provide ongoing or predetermined changes/adaptations to the scanning process based on already scanned teeth.

Computer System for Guiding an Intra-Oral Scan

Having described a system 1 for guiding an intra-oral scan using augmented reality, reference will now be made to FIG. 4, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the disclosure using other computer systems and/or architectures.

In one example embodiment herein, the computer system 100 may include at least one computer processor 122 and may include a tracking system 2, user interface 126 and input unit 130. The input unit 130 may be used by to send information to the computer processor 122. In one exemplary embodiment herein, the input unit 130 is a finger or stylus to be used on a touchscreen interface (not shown). The input unit 130 may alternatively be a gesture/voice recognition device, a trackball, a mouse or other input device such as a keyboard or stylus. In one example, a display unit 128, the input unit 130, and the computer processor 122 may collectively form the user interface 126.

The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive a request for a scan strategy 42 and may obtain instructions concerning the request from one or more storage units of the computer system 100. The processor 122 may then load said instructions and execute the loaded instructions such as routing the scan strategy 42 to a screen of the display device 12 such that the scan strategy 42 may be overlaid on the target site 14a such that said scan strategy 42 appears directly superimposed on said target site 14a. In yet another alternative embodiment of the present invention, the computer system may use projection based augmented reality systems wherein, for example, a projector and depth sensors, along with the tracking system 2 and/or markers on the patient 14 (e.g. hidden markers) may be used to project the scan strategy 42 directly onto target sites 14a (e.g. buccal cavity) of the patient. Herein, the display device 12 such as augmented reality glasses may not be needed to view the projected scan strategy 42

One or more steps/procedures for visually communicating the scan strategy 42 to the clinician 10 may be stored on a non-transitory storage device in the form of computer-readable program instructions. To execute a procedure, the processor 122 loads the appropriate instructions, as stored on a storage device, into memory and then executes the loaded instructions as shown in FIG. 4 discussed hereinafter.

The computer system 100 may further comprise a main memory 132, which may be a random access memory ("RAM") and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or a wireless interface), a communications port (e.g., a Universal Serial Bus ("USB") port or a FireWire® port), a Personal Computer Memory Card International Association ("PCMCIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described hereinafter.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the system for guiding an intra-oral scan, to perform all or some of the some of the methods described herein.

Implementation of other hardware arrangement so as to perform the functions described herein will be apparent to persons skilled in the relevant art(s) in view of this description.

Method for Guiding an Intra-Oral Scan.

Figure 4:
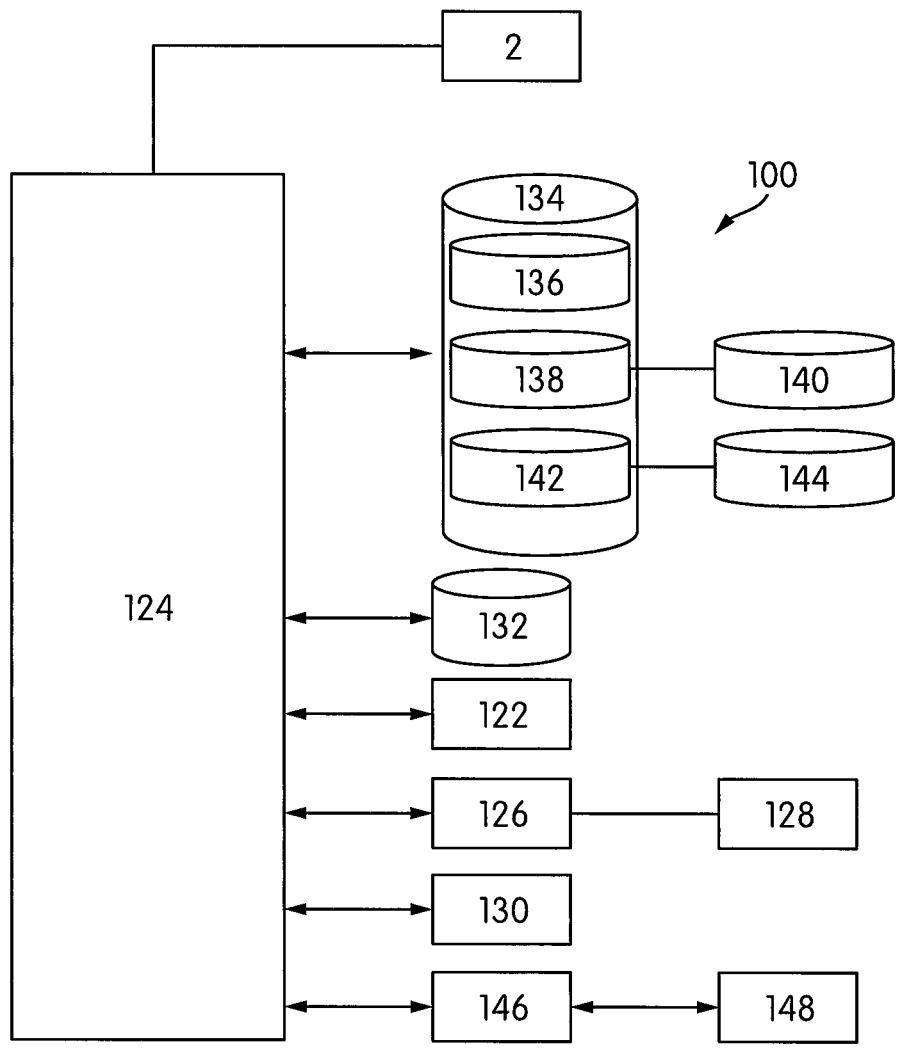
FIG. 4 is a block diagram showing a computer system according to an embodiment of the present invention.

Having described the computer system 100 of FIG. 4, methods for guiding an intra-oral scan will now be further described in conjunction with FIGS. 5-13.

Figure 5:
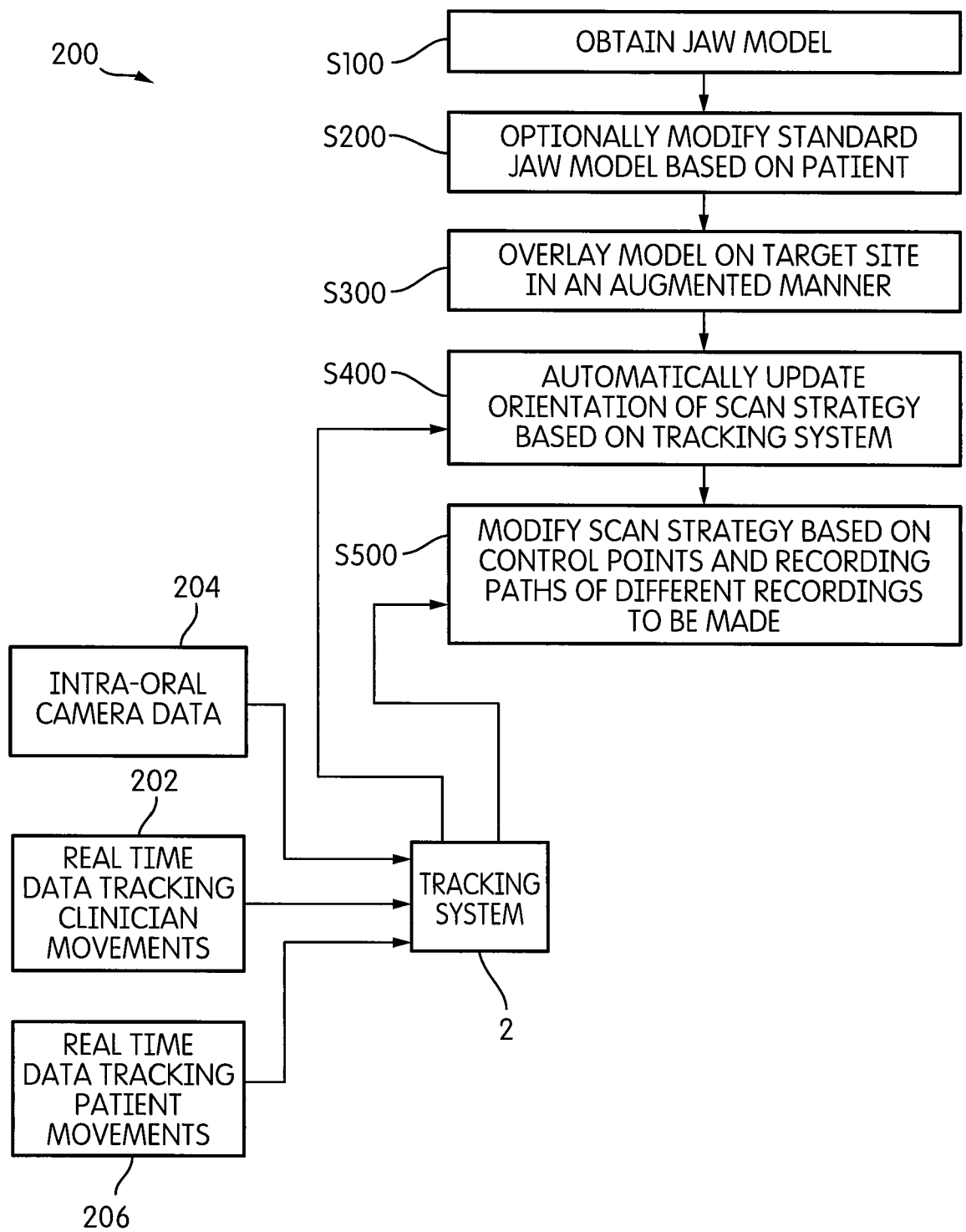
FIG. 5 is a flow chart showing a method according to an exemplary embodiment of the present invention.

FIG. 5 shows a process 200 for guiding an intra-oral scan. The process may begin by obtaining a jaw model 26 as shown in Step S100. The jaw model may be a standard three-dimensional jaw model 26a or an ongoing three dimensional reconstruction of scanned teeth 26b.

In an embodiment in which the obtained jaw model 26 is a standard three-dimensional jaw model 26a, said standard three-dimensional jaw model 26a, may be modified (Step S200) to correspond to a tooth situation of the patient 14. For example, if specific teeth of the patient's jaw are determined to be missing (such as the back molars with the Federation Dentaire Internationale (FDI) numbers 18, 28, 38 or 48), these teeth may also be removed from the standard jaw model, thereby enabling the clinician 10 to establish a one-to-one correspondence between actual teeth 17 of the patient 14 and model teeth 17a of the standard three-dimensional jaw model 26a. However, the standard three-dimensional jaw model 26a may preferably be obtained based on images of the actual teeth 17 of the patient 14 obtained through the camera system 3. For example, using object recognition on images of the intra-oral cavity 22 of the patient 14 obtained by the camera system 3, anatomical features of said intra-oral cavity 22 (such as cusp, fissures, ridges, gums etc. or the lack thereof) may be used to determine which teeth are present or missing. Based on the analysis, the standard three-dimensional model 26a may be modelled after said images or a predetermined standard model of human teeth may be modified to correspond to the actual teeth 17 of the patient 14.

In an embodiment in which the obtained jaw model 26 is an ongoing three-dimensional reconstruction of scanned teeth 26b, the jaw model 26 may begin as a standard three-dimensional jaw model 26a and portions of the standard three-dimensional jaw model 26a corresponding to actual teeth 17 of the patient 14 that have been scanned and successfully registered may be replaced/covered/overlaid with a three-dimensional reconstruction of the corresponding three dimensional optical recordings 4 obtained by the intra-oral camera 16. In a further embodiment, the ongoing three-dimensional reconstruction of scanned teeth 26b may begin as an empty model and may be filled in continuously by the three-dimensional reconstruction of the three-dimensional optical recordings 4 that are being acquired.

In an embodiment in which the obtained jaw model 26 is a standard three-dimensional jaw model 26a, an ongoing three-dimensional reconstruction of teeth that are being scanned may also be separately displayed alongside the standard three-dimensional jaw model 26a in the field of view 32 of the clinician 10 to indicate progress.

In Step S300, the jaw model 26 may be overlaid in an augmented manner over the target site 14a as part of the scan strategy 42. Thereafter, an orientation of the jaw model 26 (and thus the scan strategy 42) may be continuously updated in real-time based on the real time data from the tracking system 2 tracking patient movements 206 and clinician movements 202. (Step S400).

In Step S500, the scan strategy 42 may be modified to guide the clinician in performing an intra-oral scan using one or more control points 13, 15, 42, 55, 57, 60, 61, 73, 93, 94, 96, 97 and one or more recording paths (34, 41, 51, 62, 72, 74, 76, 92, 95) which may be displayed over the jaw model 26 as discussed hereinafter and in FIGS. 6-13. Herein, the computer system 100 may be in communication with the intra-oral camera 16 being used by the clinician 10 for the scan procedure. Based on obtained three-dimensional optical recordings 4, and confirmations of the control points, the scan strategy 42 may be modified as follows.

Figure 6:
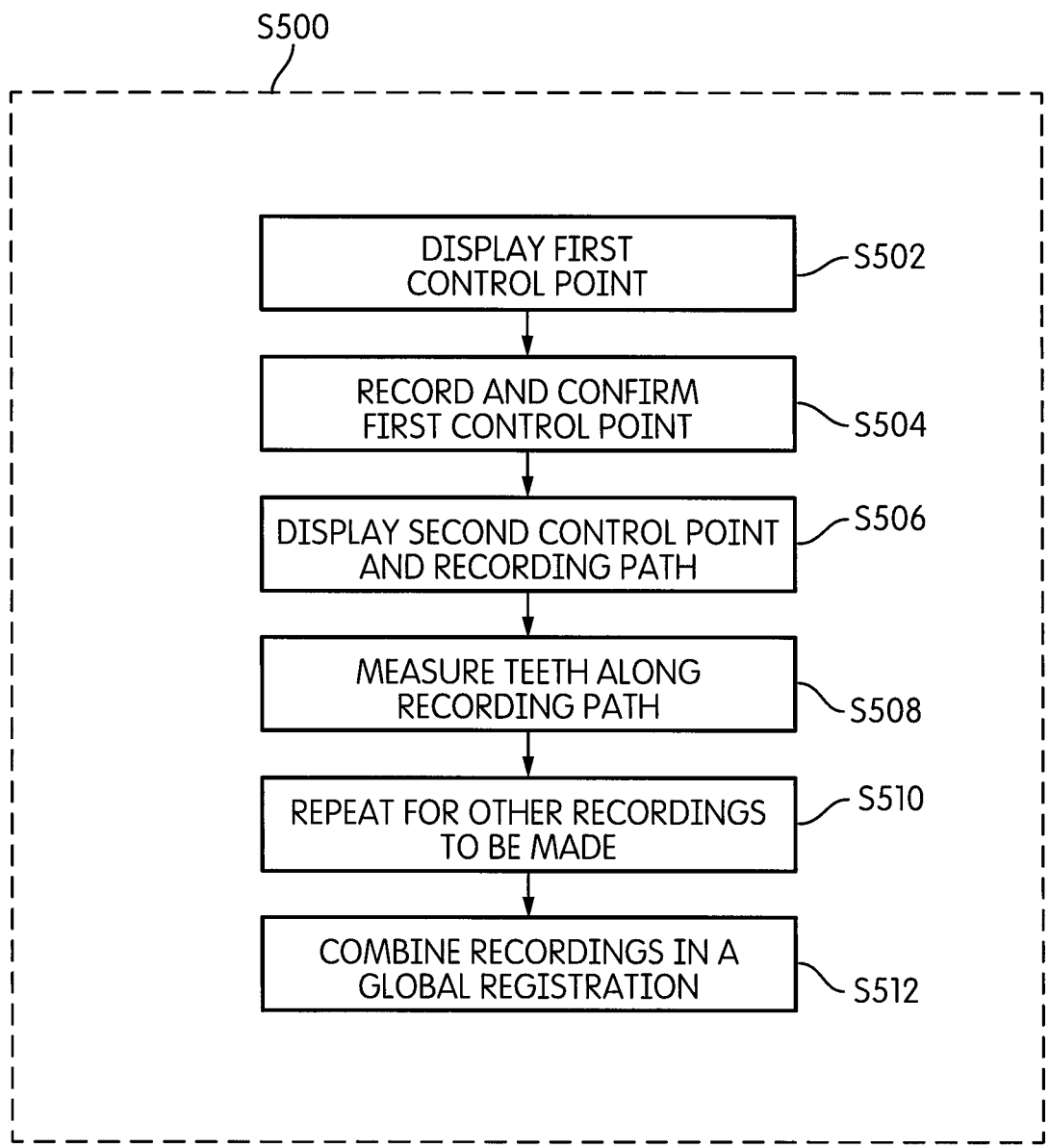
FIG. 6 is a flow chart showing a further method according to an exemplary embodiment of the present invention.

As shown in FIG. 6, a first control point 13 (shown in FIG. 3a) may be displayed on the jaw model 26 in the middle of an occlusal surface 8 of a model teeth 17a, e.g. molar 9 in Step S502. The first control point 13 is represented schematically as a black circle. The clinician 10 may then move the intra-oral camera 16 in an area of the molar 9 so that the camera records the first control point 13. The intra-oral camera 16 may be held steadily over the first control point 13 for a predetermined period of time until an acoustic, visual and/or haptic signal ensues as a feedback and the position of the first control point is thereby confirmed (Step S504). The feedback may be based on an adequacy of obtained three-dimensional optical recordings 4 (such as adequate overlap, adequate exposure time, etc.). The first control point 13 may also be confirmed manually by operating a button 11 on the intra-oral camera 16. Alternatively, the control point 10 can also be confirmed by means of the input unit 130 (FIG. 4) which may be for example, a gesture/voice recognition device.

A second control point 15 and a recording path 23 may be displayed in addition to the first control point 13 (Step S506). The displayed recording path 23 may serve as a user guidance for the clinician 10 in order to display which areas of actual teeth 17 are to be measured. The actual teeth 17 are then measured/scanned along the recording path 34 in Step S508 to obtain a first cluster. Scanned teeth may be marked in the scan strategy 42 (for example, they may be colored differently from unscanned teeth) as a further guidance for the clinician 10. The measurement may then be repeated (Step S510) for other clusters using other control points and other recording paths as described hereinafter. The clusters may then be combined in a global registration step using shared overlapping areas in Step S512.

In an embodiment in which the jaw model 26 is not overlaid on the actual teeth, the jaw model 26 may be pivoted in the field of view 32 such that buccal surfaces 20 of a recording area 33 (which is shown as a dashed line) that are to be recorded are displayed in the foreground, wherein the previously measured occlusal surfaces 8 may also be visible. Herein, a line of sight on the jaw model 42 may be changed during the measurement according to the movement of the intra-oral camera 16.

FIGS. 7-13 depicts scan strategies 42 overlaid in an augmented manner on a target site 14a or in a field of view 32 of the clinician 10 wherein the scan strategies 42 may be used in guiding the recording of the patient's actual teeth 17.

Figure 7:
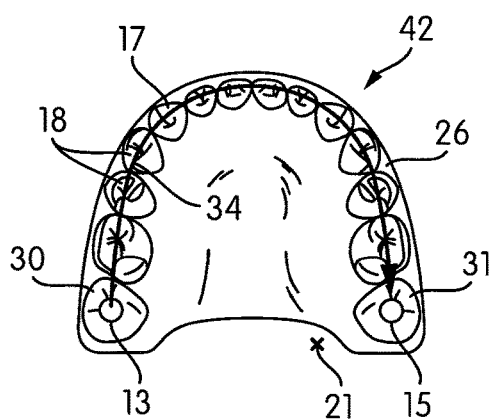
FIG. 7 a top view of a scan strategy for an occlusal measurement.
Figure 8:
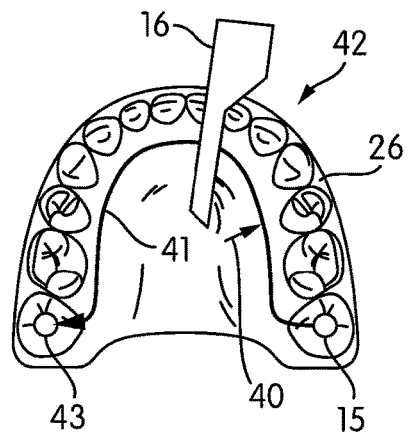
FIG. 8 a top view of a scan strategy for a lingual measurement.

FIG. 7 depicts a scan strategy 42 (including a jaw model 26) for an upper jaw, wherein a first recording path 34 originating from the first control point 13 on a first molar 30 with the FDI number 37 runs up to the second control point 15 on the opposing end of the jaw arch on the second molar 31 having the FDI number 47. The first recording path 34 thereby runs through the tooth centers 18 of the model teeth 17*a* of the jaw model 26. The intra-oral camera 16 may therefore be moved such that centers of the three-dimensional optical recordings 4 coincide or substantially coincide with the first recording path 34. In this way, an occlusal measurement may therefore carried out from an occlusal direction of the top jaw. FIG. 8 depicts a scan strategy 42 illustrating the guidance of a lingual measurement of the upper jaw from a lingual or oral direction 40. The intra-oral camera 16 may be positioned relative to the actual teeth 17 in such a way that the recording from the lingual direction 40 may be carried out along a second recording path 41 originating from the second control point 15 toward a third control point 43. Therefore, the inside tooth surfaces of the upper jaw may be measured with the lingual measurement.

Figure 9:
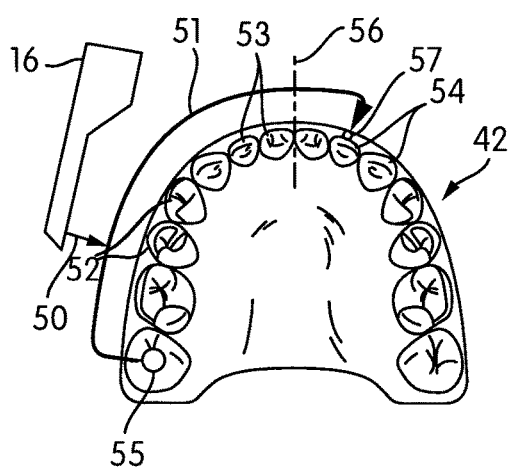
FIG. 9 is a top view of a scan strategy for a first step of a buccal measurement.

FIG. 9 depicts a scan strategy 42 illustrating the guidance of a buccal measurement from a buccal direction 50, wherein the intra-oral camera 16 may be pivoted around the jaw in such a way that the buccal tooth surfaces 52 and the labial tooth surfaces 53 are measured. The teeth 54 may therefore not be measured in the first step. The third recording path 51 may thereby originate from a fourth control point 55 at the molar having the FDI number 37 across a middle 56 of the jaw arch up to a fifth control point 57. The position of the fourth control point 55 may thereby correspond to the position of the control point 43 and the control point 13.

Figure 10:
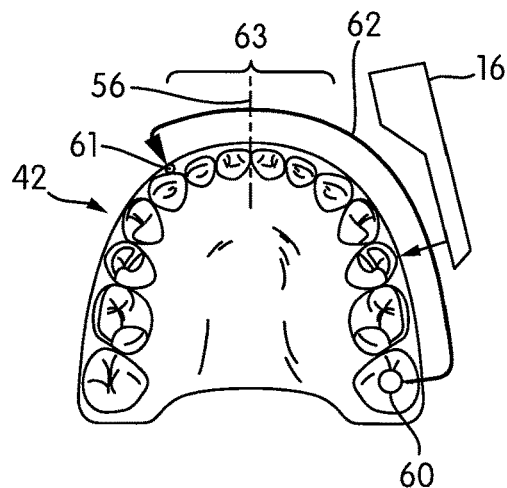
FIG. 10 is a top view of a scan strategy for a second step of a buccal measurement.

FIG. 10 depicts a scan strategy 42 showing a second buccal measurement originating from a sixth control point 60 across the middle 56 of the jaw arch to a seventh control point 61 along a fourth recording path 62. A first cluster from the first buccal measurement from FIG. 9 and a second cluster from the second buccal measurement from FIG. 10 may be registered to one another using a shared overlapping area 63 in the middle of the jaw arch.

Figure 11:
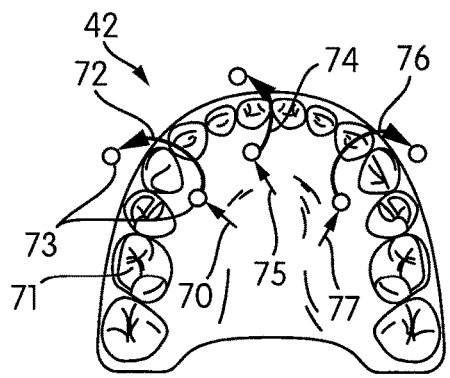
FIG. 11 is a top view of a scan strategy illustrating a plurality of fringe recording sequences.

FIG. 11 shows a scan strategy 42 illustrating first fringe recording sequence in buccal direction 70 perpendicular to a jaw curve 71 of the jaw arch to be measured along a fifth recording path 72 between the control points 73. The fifth recording path 72 may thereby run in the area of a molar with the FDI number 14. In addition, a second fringe recording sequence may be performed in the labial direction 75 along a sixth recording path 74 in the area of the incisor with the FDI number 11, and a third fringe recording sequence may be performed in the buccal direction 77 along the seventh recording path 76 in the area of the molar with the FDI number 24.

Figure 12:
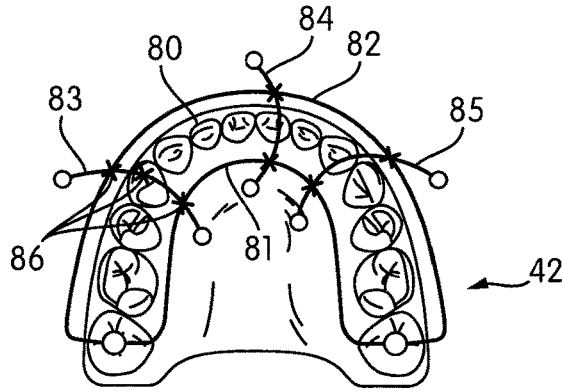
FIG. 12 is a sketch illustrating a linking of the different clusters.

FIG. 12 depicts a sketch showing that a first cluster 80 from the occlusal measurement in FIG. 7, a second cluster 81 from the lingual measurement in FIG. 8 and a third cluster 82 from the buccal direction in FIG. 9 and FIG. 10 are linked to each other by the fourth cluster 83 of the first fringe recording sequence from FIG. 11, as well as by the fifth cluster 84 of the second fringe recording sequence and the sixth cluster 85 of the third fringe recording sequence. The linkage points 86 are indicated by the crosses.

Figure 13:
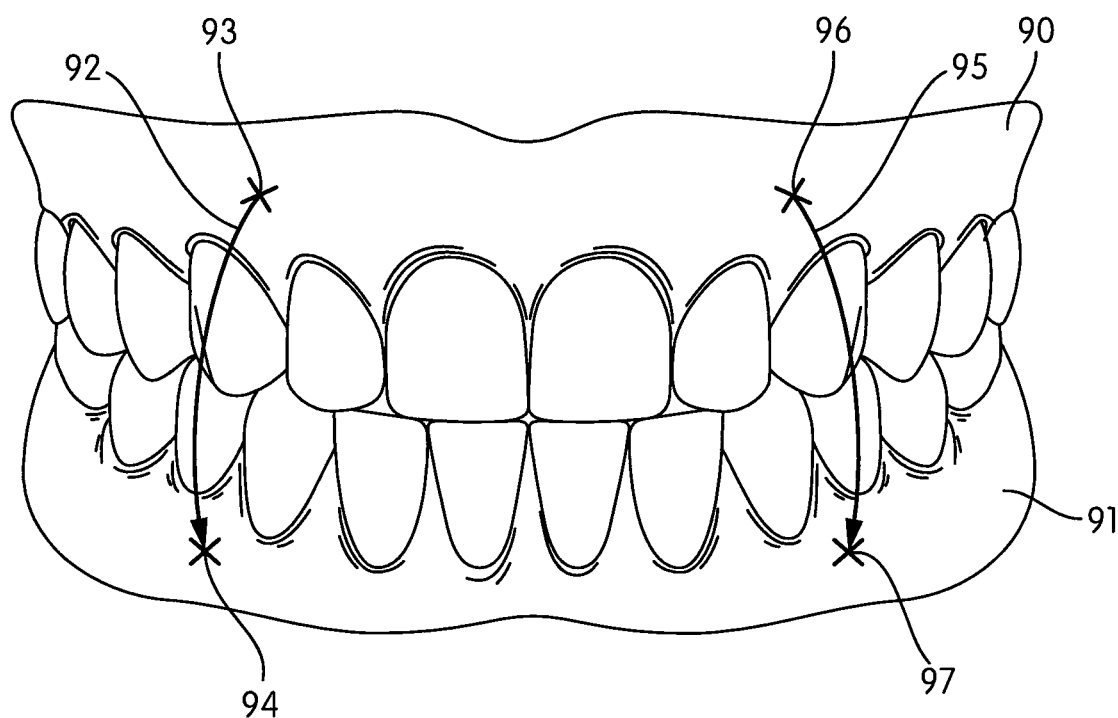
FIG. 13 is a top view of a scan strategy illustrating a bite block registration.

FIG. 13 depicts a scan strategy 42 to illustrate a bite block registration, wherein a first three-dimensional model 90 of the upper jaw may be registered relative to a second three-dimensional model 91 of the lower jaw. In this way, a first buccal recording sequence may be performed along a recording path 92 between the control points 93 and 94, and a second buccal recording sequence may be performed along the recording path 95 between a control point 96 and a control point 97. The first buccal recording sequence may thereby run in the area of the teeth with the FDI numbers 14 and 44. The second buccal recording sequence may run in the area of the teeth with the FDI numbers 24 and 34.

In a further embodiment of the present invention, a palate measurement may be performed. Herein, a 3D intraoral scan may be combined with images from the camera system 3 (such as images of the palate taken by the display device 12 for augmented visualization) in order to create dentures. A digital impression may be inadequate for obtaining scans of the gingivobucal/mucolabial fold. However by combining images of the gingivobucal/mucolabial fold taken with the display device adequate information may be obtained for denture design/fabrication.

In view of the foregoing description, it may be appreciated that the example embodiments described herein provide a method, system and computer readable storage media for guiding an intra-oral scan.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

The invention claimed is:

1. A method for guiding a scan of a jaw utilizing augmented visualization, the method comprising:
   obtaining a jaw model, the jaw model being a standard three-dimensional jaw model;
   providing a scan strategy including the jaw model and a first and second control points;
   overlaying the scan strategy as an augmentation on a target site in a patient's mouth through a display device including a head mounted augmented reality glass for augmented visualization such that the scan strategy appears directly superimposed on said target site;
   determining a recording path based on the first and second control points;
   acquiring a plurality of three-dimensional optical recordings from an intra-oral camera when the intra-oral camera is moved over the jaw along the determined recording path such that a corresponding region of the jaw defined by the determined recording path is recorded; and
   registering the plurality of three-dimensional optical recordings into an overall three-dimensional recording
   wherein responsive to scanning and successfully registering portions of the standard three-dimensional jaw model corresponding to actual teeth of the patient, replacing the portions with an ongoing three-dimensional reconstruction of the corresponding three dimensional optical recordings obtained by the intra-oral camera.

2. The method according to claim 1, wherein said standard three-dimensional jaw model is modified to correspond to a tooth situation of the patient.

3. The method according to claim 1, wherein the scan strategy is overlaid to guide a measurement process selected from the group consisting of an occlusal measurement, a lingual measurement, a first step of a buccal measurement, a second step of a buccal measurement, a fringe measurement, a bite block measurement and a palate measurement.

4. The method according to claim 1, wherein the scan strategy is automatically updated in order to record different portions of the jaw.

5. The method according to claim 1, further comprising determining areas of the plurality of three-dimensional optical recordings that have gaps, and providing additional control points and/or additional recording paths on the scan strategy in succession for further recording.

6. The method according to claim 1, wherein a success of the registering step is tracked in order to update the scan strategy.

7. The method according to claim 1, further comprising updating an orientation of the scan strategy in real time based on a tracking system, said tracking system including at least one of information from the intra-oral camera, information tracking patient movements and/or information tracking clinician movements.

8. The method according to claim 1, wherein said target site is a site selected from the group consisting of the actual teeth, or a site in a field of view of a user of the display device for augmented visualization.

9. A system for guiding a scan of a jaw utilizing augmented visualization, the system comprising:
   a display device for augmented visualization, and
   at least one processor configured to;
   obtain a jaw model, the jaw model being a standard three-dimensional jaw model;
   provide a scan strategy including the jaw model and a first and second control points;
   overlay the scan strategy as an augmentation on a target site in a patient's mouth through a display device including a head mounted augmented reality glass for augmented visualization such that the scan strategy appears directly superimposed on said target site;
   determine a recording path based on the first and second control points;
   acquire a plurality of three-dimensional optical recordings from an intra-oral camera when the intra-oral camera is moved over the jaw along the determined recording path such that a corresponding region of the jaw defined by the determined recording path is recorded; and
   register the plurality of three-dimensional optical recordings into an overall three-dimensional recording;
   wherein responsive to scanning and successfully registering portions of the standard three-dimensional jaw model corresponding to actual teeth of the patient, replacing the portions with an ongoing three-dimensional reconstruction of the corresponding three dimensional optical recordings obtained by the intra-oral camera.

10. The system according to claim 9, wherein the processor is further configured to modify the standard three-dimensional jaw model to correspond to a tooth situation of the patient.

11. The system according to claim 9, wherein the processor is further configured to overlay the scan strategy to guide a measurement process, said measurement process being selected from the group consisting of an occlusal measurement, a lingual measurement, a first step of a buccal measurement, a second step of a buccal measurement, a fringe measurement, a bite block measurement and a palate measurement.

12. The system according to claim 9 wherein the processor is further configured to update the scan strategy automatically in order to record different portions of the jaw.

13. The system according to claim 9, wherein the processor is further configured to perform the steps of determining areas of the plurality of three-dimensional optical recordings that have gaps, and providing additional control points and/or additional recording paths on the scan strategy in succession for further recording.

14. The system according to claim 9 wherein the processor is further configured to track a success of the registering step in order to update the scan strategy.

15. The system according to claim 9, further comprising the processor is further configured to perform the step of updating an orientation of the scan strategy in real time based on a tracking system, said tracking system including at least one of information from the intra-oral camera, information tracking patient movements and/or information tracking clinician movements.

16. The system according to claim 9, wherein said target site is a site selected from the group consisting of the actual teeth, or a site in a field of view of a user of the display device for augmented visualization.

17. A non-transitory computer-readable storage medium storing a program which, when executed by a computer system, causes the computer system to:
   obtain a jaw model, the jaw model being a standard three-dimensional jaw model;
   provide a scan strategy including the jaw model and a first and second control points;
   overlay the scan strategy as an augmentation on a target site in a patient's mouth through a display device including a head mounted augmented reality glass for augmented visualization such that the scan strategy appears directly superimposed on said target site;
   determine a recording path based on the first and second control points;
   acquire a plurality of three-dimensional optical recordings from an intra-oral camera when the intra-oral camera is moved over the jaw along the determined recording path such that a corresponding region of the jaw defined by the determined recording path is recorded; and
   register the plurality of three-dimensional optical recordings into an overall three- dimensional recording;
   wherein responsive to scanning and successfully registering portions of the standard three-dimensional jaw model corresponding to actual teeth of the patient, replacing the portions with an ongoing three-dimensional reconstruction of the corresponding three dimensional optical recordings obtained by the intra-oral camera.

* * * * *

UNITED STATES PATENT AND TRADEMARK OFFICE
CERTIFICATE OF CORRECTION

PATENT NO. : 12,303,110 B2
APPLICATION NO. : 17/425964
DATED : May 20, 2025
INVENTOR(S) : Koza et al.

Page 1 of 1

It is certified that error appears in the above-identified patent and that said Letters Patent is hereby corrected as shown below:

In the Claims

In Column 13, Line 25, in Claim 7, delete "and/or" and insert --and-- therefor

In Column 14, Line 27, in Claim 15, delete "and/or" and insert --and-- therefor

In Column 14, Line 55, in Claim 17, delete "three- dimensional" and insert --three-dimensional-- therefor Signed and Sealed this
Twenty-second Day of July, 2025

Coke Morgan Stewart
*Acting Director of the United States Patent and Trademark Office*